United States Patent [19]

Gregory et al.

[11] 4,305,502
[45] Dec. 15, 1981

[54] PHARMACEUTICAL DOSAGE FORM PACKGES

[75] Inventors: George K. E. Gregory, Marlow; David S. S. Ho, Maidenhead, both of England

[73] Assignee: John Wyeth & Brother Limited, Maidenhead, England

[21] Appl. No.: 925,002

[22] Filed: Jul. 14, 1978

[30] Foreign Application Priority Data

Jul. 20, 1977 [GB] United Kingdom ............... 30399/77

[51] Int. Cl.³ .......................... B65D 85/56; B65B 7/28
[52] U.S. Cl. .......................................... 206/532; 34/5; 53/432; 53/452; 53/559; 156/69; 156/80; 156/292; 206/484; 206/538; 264/28; 264/101; 424/22; 428/72
[58] Field of Search ............... 34/5; 53/122, 432, 440, 53/452, 559; 128/272; 156/69, 80, 155, 292; 206/538, 484, 531, 532, 539; 239/60; 264/28, 101; 424/14, 22; 428/72, 913

[56] References Cited

U.S. PATENT DOCUMENTS 2,834,456  5/1958  Langer ............................ 206/531 X
3,059,766 10/1962  Jordt ................................ 206/538 X
3,124,913  3/1964  Arcudi et al. ......................... 53/440
3,234,091  2/1966  Lang et al. ............................. 424/14
3,504,788  4/1970  Gray .................................... 206/531
3,894,896  7/1975  Watanabe ............................. 156/69
3,924,748 12/1975  Braverman ...................... 206/538 X
3,933,559  1/1976  Watanabe ....................... 206/538 X
4,039,080  8/1977  Cappuccilli ..................... 206/538 X
4,228,215 10/1980  Hein et al. ......................... 428/72 X

FOREIGN PATENT DOCUMENTS 1310824  3/1973  United Kingdom .
1447988  9/1976  United Kingdom .

Primary Examiner—Robert A. Dawson
Attorney, Agent, or Firm—Arthur E. Wilfond

[57] ABSTRACT

The invention relates to packages containing shaped articles carrying chemicals, particularly to pharmaceutical dosage forms carrying pharmaceuticals. The shaped articles, which disintegrate rapidly in water are contained in depressions in sheets of filmic material and are enclosed by a covering sheet adhering to the filmic material. The shaped articles may be formed in the depressions by a sublimation process.

10 Claims, 3 Drawing Figures

PHARMACEUTICAL DOSAGE FORM PACKGES

This invention relates to packages and more particularly to packages containing shaped articles comprising pharmaceuticals or chemical reagents and to processes for preparing such packages.

Many pharmaceuticals are administered orally in the form of solid shaped articles such as tablets, pills and capsules. Generally the tablet, pill or capsule has to be swallowed from the mouth to the stomach to enable the pharmaceutical to be absorbed in the gastro-enteric system. However, in some cases there is the problem that swallowing is difficult or not feasible. Some subjects, particularly paediatric and geriatric patients, may be unco-operative and spit the tablet out instead of swallowing it. A similar difficulty can be present in administering pharmaceuticals to non-human animals in veterinary treatment in that animals may also be unco-operative about taking tablets. The invention disclosed in the specification of U.S. application Ser. No. 837,345 filed Sept. 28, 1977 for "Articles for carrying chemicals" seeks to avoid this problem by providing a pharmaceutical dosage form that disintegrates rapidly in the mouth.

In addition, it is often desired to add a predetermined amount of chemical (not necessarily a pharmaceutical) to an aqueous medium. For example, the chemical may be a diagnostic compound which it is desired to add to a biological sample, such as a sample of urine or blood, for determining the amount of a particular constituent present in the sample. Alternatively, it may be desired to add a predetermined amount of chemical reagent to a known amount of aqueous liquid to produce a standarised liquid which can be used, for example, in chemical analysis. Again the chemical may be a water-soluble or water-disperisble pharmaceutical which can be added to a known amount of aqueous medium to form a pharmaceutical solution or dispersion which can be used in the usual way for administering the pharmaceutical such as by injection or inhalation. Further, certain chemicals are difficult or hazardous to handle in solution or suspension and it may be desirable to convert them into solid form which can be subsequently added to an aqueous medium to produce a solution or dispersion of the chemical. In all these instances it is desirable that when the chemical is added to the aqueous medium the chemical should dissolve rapidly or be dispersed uniformly throughout the medium. The specification of the above-mentioned application discloses a shaped article carrying a chemical in which the shaped article is capable of being rapidly disintegrated by water. According to the prior specification the shaped article comprises an open matrix network carrying the chemical, the open matric network being comprised of a water-soluble or water-dispersible carrier material that is inert towards the chemical.

Preferably the shaped article is a pharmaceutical dosage form carrying a pharmaceutical substance.

By "rapidly disintegrated" as used herein and also in the aforementiond specification is meant that the shaped articles are disintegrated in water within 10 seconds. Preferably the shaped article disintegrates (dissolves or disperses) within 5 seconds or less. The disintegration time is measured by a procedure analogous to the Disintegration Test for Tablets, B.P. 1973. The procedure is described below:

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve.

A glass cylinder with a flat base and an internal diameter of about 45 mm containing water not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remains clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it. No such particle should remain after 10 seconds.

By the term "open matrix network" as used herein and in the aforementioned specification there is meant a network of water-soluble or water-dispersible carrier material having interstices dispersed throughout. The open matrix network of carrier material is of generally low density. For example the density may be within the range 10 to 200 mg/cc e.g. 10 to 100 mg/cc, preferably 30 to 60 mg/cc. The density of the shaped article may be affected by the amount of pharmaceutical substance or other chemical, or any other ingredients, incorporated into the article and may be outside the above-mentioned preferred limits for the density of the matrix network. The open matrix network which is similar in structure to a solid foam enables a liquid to enter the product through the interstices and permeate through the interior. Permeation by aqueous media exposes the carrier material of both the interior and exterior of the product to the action of the aqueous media whereby the network of carrier material is rapidly disintegrated. The open matrix structure is of a porous nature and enhances disintegration of the product as compared with ordinary solid shaped pharmaceutical dosage forms such as tablets, pills, capsules, suppositories and pessaries. Rapid disintegration results in rapid release of any pharmaceutical substance or other chemical carried by the matrix.

The carrier material of the shaped article may be any water-soluble or water-dispersible material that is pharmacologically acceptable or inert to the chemical and which is capable of forming a rapidly disintegratable open matrix network. Preferaby water-soluble material is used as the carrier since this results in the most rapid disintegration of the matrix when the product is placed in an aqueous medium. A particularly advantageous carrier may be formed from polypeptides such as gelatin, particularly gelatin which is partially hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferaby used at concentrations of about 1 to 6% weight/vol., most preferably at 2 to 4% e.g. about 3%. Other carrier materials may be used in place of partially hydrolysed gelatin for example polysaccharides such as hydrolysed dextran, dextrin and alginates (e.g. sodium alginate) or mixtures of above mentioned carriers with each other or with other carrier materials such as polyvinyl alcohol, polyvinylpyrrolidine or acacia.

The pharmaceutical dosage forms may be employed to administer a wide variety of pharmaceutical substances as described in the aforementioned specification.

The shaped articles may incorporate ingredients in addition to the chemical or pharmaceutical substance as described in the aforementioned specification. For example the pharmaceutical dosage form of the present invention may incorporate pharmaceutically acceptable adjuvants. Such adjuvants include, for example, colouring agents, flavouring agents, preservatives (e.g. bacteriostatic agents), and the like.

According to the aforementioned specification, the shaped articles are prepared by a process which comprises subliming solvent from a composition comprising the chemical (e.g. pharmaceutical substance) and a solution of the carrier material in a solvent, the composition being in the solid state in a mould.

According to the aforementioned specification the sublimation is preferably carried out by freeze drying a composition comprising the chemical (e.g. pharmaceutical substance) and a solution of the carrier material in a solvent. The composition may include additional ingredients, such as those mentioned above. The solvent is preferably water but it may contain a cosolvent (such as an alcohol e.g. tert-butyl alcohol) to improve the solubility of the chemical. The composition may also contain a surfactant e.g. Tween 80 [polyoxyethylene (20) sorbitan mono-oleate]. The surfactant may help to prevent the freeze dried product sticking to the surface of the mould. It may also aid in the dispersion of the chemical.

The mould, according to the aforementioned specification is preferably made of metal and has a series of cylindrical or other shape depressions in it, each of a size corresponding to the desired size of the shaped article to be produced. After freeze drying in such a mould the shaped articles are removed and then suitably stored, for example in airtight jars.

We have now found a novel method of preparing the shaped articles which avoids transferring them from metal moulds to suitable storage containers. Since the shaped articles are rather fragile it is an advantage to restrict handling of them to a minimum. The present invention avoids transferring the shaped article from a mould to a suitable storage container by employing, as the mould, depressions in a sheet of filmic material and then adhering a covering sheet around the depressions to enclose the shaped articles. Accordingly the present invention provides a process for preparing packages containing one or more shaped articles carrying chemicals (e.g. pharmaceutical substances), as hereinbefore described, which process comprises subliming solvent from a composition comprising chemical (e.g. the pharmaceutical substance) and a solution of the carrier material in a solvent, the composition being in the solid state in one or more depressions in a sheet of filmic (filmy) material, and then adhering a covering sheet around the depressions to enclose the shaped articles in the depressions. The process of the invention enables packages of the shaped articles to be produced in which handling of the individual shaped articles may be eliminated until the user, e.g. the patient in the case of a shaped article comprising a pharmaceutical substance, removes the product from the depression in the package immediately prior to use.

The sublimation is preferably carried out by freeze drying a composition comprising the pharmaceutical substance or chemical reagent and a solution of the carrier material in a solvent, e.g. water.

The invention also provides a package comprising a sheet of filmic material having one or more depressions therein, one or more of the depressions containing a shaped article (as hereinbefore described), and a covering sheet adhering to the sheet of filmic material so as to enclose the shaped article or articles.

An embodiment of the package of the invention is illustrated in the accompanying drawings in which.

Figure 1:
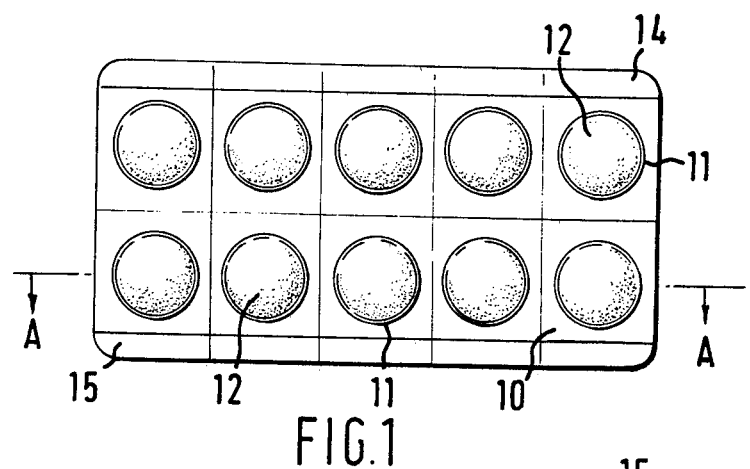
FIG. 1 is a plan view of the upper surface of the package.
Figure 2:
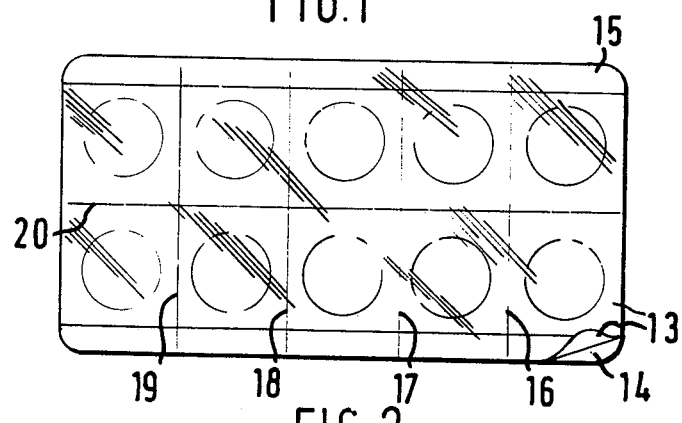
FIG. 2 is a plan view of the lower surface of the package of FIG. 1.
Figure 3:
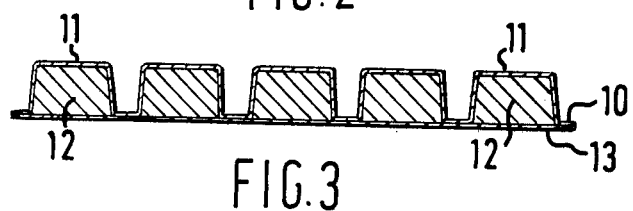
FIG. 3 is a cross sectional view taken along the line A—A of FIG. 1.

In the drawings the filmic material 10 is transparent and contains ten depressions 11, each of which contains a shaped article 12. A covering sheet 13 adheres to the under surface of the filmic material 10 to enclose the shaped articles. In general, the filmic material and the covering sheet may, for example, be similar to those employed in conventional blister packs used for packaging tablets and like medicament forms. For example, the filmic material is usually a suitable stiff but resilient film and it is normally stronger than the covering layer. Preferably the filmic material is made of thermoplastic material so that the depressions may be formed by, for example, thermoforming. The filmic material may, for example, be a polyvinyl chloride film or a laminate such as a polyvinylchloride/polyvinylidenechloride, polyvinylchloride/polytetrafluoroethylene or polyvinylchloride/polyvinylidenechloride/polyethylene. The shaped articles are moisture sensitive and therefore it may be advisable to use a thermoplastic material which is particularly moisture resistant or to use a non-thermoplastic moisture-resistant filmic material, for example a stiff aluminium foil in which the depressions can be formed by cold pressure forming. Alternatively if the shaped articles are particularly moisture-sensitive the complete package may be enclosed in a removable moisture-resistant outer case, e.g. an aluminium foil bag.

The covering sheet is preferably an aluminium foil or aluminium foil laminate (e.g. aluminium foil/paper) which may be adhered to the filmic material around the depressions by, for example, a heat sensitive adhesive material. The shaped articles are rather fragile and it is not generally possible to remove them from the package by forcing them through the covering sheet, as with conventional blister packs, unless the covering sheet is relatively thin. Accordingly, the covering sheet is preferably adhered to the filmic material such that it may be peeled away from the filmic material by the user to expose the shaped articles in their depressions. For example in the package shown in the drawings, in the portions 14 and 15 at the sides, the covering sheet is not adhered to the filmic material so that the user may start peeling away the covering sheet at these locations. Preferably the covering sheet around one or more of the depressions is inherently weakened by, for example, surface perforations (as shown for example in the drawings by perforations 16, 17, 18, 19, 20) so that the covering sheet may be removed in stages to expose the shaped articles in succession. The user may thus remove the individual shaped articles from the package as desired. The covering sheet may be made of a material other than aluminium foil or aluminium foil laminate (such as a plastic film), if it adheres by peelable means to the filmic material. The composition may be freeze dried in the depressions of the filmic material by, for example, procedures analogous to those described in the aforementioned specification. For example, a measured quantity of the composition may be added to each depression and the filmic material containing the filled depressions then cooled with a cooling medium e.g. liquid nitrogen or preferably solid carbon dioxide. When the contents of the depressions are frozen the filmic material and contents may be subjected to reduced pressure and, if desired, controlled application of heat to aid the sublimation. The pressure can be below about 4 mm Hg; we prefer to employ pressures of below 0.3 mm Hg, for example 0.1 to 0.2 mm. A large sheet of filmic material (equivalent in size to many of the desired finished packages) containing numerous depressions may be subjected to the freeze drying procedure and the covering sheet may then be adhered to it. The filmic material with the adhering covering sheet may then be cut into the desired number of finished packages each having, for example, about 6 to 25 depressions, each depression containing a shaped article.

The following examples illustrate the invention:

EXAMPLE 1

| (a) Preparation of hydrolysed gelatin solution | |
| --- | --- |
| Gelatin B.P. | 30.00 g |
| Purified water to | 1000.00 ml |

The gelatin is dissolved in the water with the aid of heat and constant stirring. The resulting solution is autoclaved at 121° C. (15 p.s.i.) for one hour. The solution is allowed to cool to room temperature.

| (b) Preparation of packages containing pharmaceutical dosage forms | |
| --- | --- |
| Lorazepam | 5 g |
| Tween 80 [polyoxyethylene(20) sorbitan monoleate] | 0.5 g |
| Sucrose | 30 g |
| Gelatine solution [from Example 1(a)] | to 1000 ml |

A p.v.c. sheet of approximate size 220×330 mm containing 150 cylindrical depressions (each depression being about 1.4 cm diameter and 0.7 cm deep) is cooled with solid carbon dioxide. The lorazepam, Tween 80 and Sucrose (flavour) are mixed with the gelatin solution and mixing continued while 0.5 ml of the solution is placed in each of the depressions. When the contents of the depressions are frozen the p.v.c. sheet is immediately placed in a vacuum chamber and a vacuum of about 0.1 mm Hg is applied for 8 hours. The sheet containing the freeze dried pharmaceutical dosage forms is then removed from the vacuum chamber and an aluminium foil is sealed to the sheet surrounding the depressions by means of a heat sensitive adhesive. The surface of the metal foil is then surface perforated around each depression. The p.v.c. sheet with its adhering metal foil is then cut into 25 packs, each pack having 6 depressions. Each depression contains a pharmaceutical dosage form containing 2.5 mg of lorazepam. The dosage forms disintegrate rapidly, in 1 to 5 seconds, when taken orally.

EXAMPLE 2

| Meptazinol | 80 g |
| --- | --- |
| Sucrose | 40 g |
| Gelatine solution [from Example 1(a)] | to 1000 ml |

The procedure of Example 1 is repeated using the above composition to give packages containing pharmaceutical dosage forms each containing 40 mg of meptazinol.

EXAMPLE 3

| Oxaprozin | 200 g |
| --- | --- |
| Sucrose | 40 g |
| 3% Hydrolysed Gelatine Solution | to 1000 ml |

The hydrolysed gelatine solution is prepared as in Example 1(a) above. The procedure of Example 1(b) above is repeated, the oxaprozin being dispersed in the gelatine solution with the aid of ultrasonic vibrations. The packages produced by the procedure contain pharmaceutical dosage forms each containing 200 mg of oxaprozin.

EXAMPLE 4

| Lorazeepam | 3.33 g |
| --- | --- |
| Sodium alginate | 15 g |
| Dextran (M.wt.approx 40,000) | 35 g |
| Dextrose | 17.5 g |
| Distilled Water | to 1000 ml |

A p.v.c. sheet of approximate size 220×330 mm containing 150 cylindrical depressions (each depression being about 1.4 cm diameter and 0.7 cm deep) is cooled with solid carbon dioxide.

3.33 g of lorazepam is suspended in the water containing 15 g sodium alginate, 35 g dextran and 17.5 g dextrose with the aid of ultrasonic vibrations. 0.75 ml of the suspension is introduced into each depression. The contents of the depressions are freeze dried and packs prepared each containing six pharmaceutical dosage forms by the procedure described in Example 1(b). Each pharmaceutical dosage form contains 2.5 mg of lorazepam.

EXAMPLE 5

| Lorazepam | 3.33 g |
| --- | --- |
| Dextrin | 50 g |
| Polyvinylpyrrolidine | 30 g |
| Tween 80 | 0.2 g |
| Distilled water | to 1000 ml |

A p.v.c. sheet similar to that in Example 1(b) is cooled with solid carbon dioxide. A mixture of the above composition is prepared by a procedure analogous to that of Example 4 and 0.75 ml of the mixture introduced into each depression in the p.v.c. sheet. The contents of the depressions are freeze dried and packs prepared each containing six pharmaceutical dosage forms by the procedure described in Example 1(b). Each pharmaceutical dosage form contains 2.5 mg of lorazepam.

EXAMPLE 6

| Lorazepam | 3.33 g |
|---|---|
| Polyvinylalcohol ((M.Wt approx 1400)) | 20 g |
| Polyvinylpyrrolidine | 20 g |
| Sucrose | 30 g |
| Tween 80 | 0.2 g |
| Distilled water | to 1000 ml |

A p.v.c. sheet similar to that in Example 1(b) is cooled with solid carbon dioxide.

20 g of polyvinylalcohol is dissolved in about 500 ml of hot distilled water and the solution then cooled. 20 g of polyvinylpyrrolidine, 30 g of sucrose and 0.2 g Tween 80 are added and the mixture shaken until all the solids are dissolved. 3.33 g of lorazepam is added and dispersed with the aid of ultrasonic vibrations. The final volume of solution is adjusted to 1000 ml with distilled water.

0.75 ml of the solution is added to each depression in the p.v.c. sheet, the contents of the depressions are freeze dried and packs prepared each containing six pharmaceutical dosage forms by the procedure described in Example 1(b). Each pharmaceutical dosage form contains 2.5 mg of lorazepam.

EXAMPLE 7

| Lorazepam | 3.33 g |
|---|---|
| Acacia | 20 g |
| Sucrose | 30 g |
| Polyvinylpyrrolidine | 30 g |
| Tween 80 | 0.2 g |
| Distilled water | to 1000 ml |

A p.v.c. sheet similar to that in Example 1(b) is cooled with solid carbon dioxide.

20 g of Acacia is placed in a dry 1000 ml volumetric flask. About 10 ml of absolute alcohol is added and the flask shaken to wet the acacia powder. 500 ml of distilled water is introduced and shaken to yield a homogeneous solution. 30 g Sucrose, 30 g polyvinylpyrrolidine, 0.2 g Tween 80 and 3.33 g lorazepam are dispersed into the solution with the aid of ultrasonic vibrations. The final volume is adjusted to 1000 ml with distilled water, 0.75 Ml of the composition is added to each depression in the p.v.c. sheet. The contents of the depressions are freeze dried and packs prepared each containing six pharmaceutical dosage forms by the procedure described in Example 1(b). Each pharmaceutical dosage form contains 2.5 mg of lorazepam.

We claim:

1. A package comprising a sheet of filmy material having one or more depressions therein; one or more of the depressions containing a shaped article molded within said one or more depressions, said shaped article carrying a pharmaceutical dosage form for oral administration as a solid, which dosage form can be rapidly disintegrated by water and comprises an open matrix network carrying a unit dosage of a pharmaceutical substance, the open matrix network comprising a pharmacologically acceptable water-soluble or water-dispersible carrier material; and a peelable covering sheet adhering to the sheet of filmy material so as to enclose the dosage form or forms.

2. A package as claimed in claim 1 wherein the carrier material comprises partially hydrolysed gelatin.

3. A package as claimed in claim 1 wherein the carrier material comprises dextrin, hydrolysed dextran or an alginate.

4. A package as claimed in claim 1 wherein the filmic material is thermoplastic material.

5. A package as claimed in claim 1 wherein the covering sheet is an aluminium foil or aluminium foil laminate.

6. A package comprising a sheet of filmy thermoplastic material having one or more depressions therein, one or more of said depressions containing a shaped article molded within said one or more depressions, said shaped article carrying a pharmaceutical dosage form for oral administration as a solid, which dosage form can be rapidly disintegrated by water and comprises an open matrix network carrying a unit dosage of a pharmaceutical substance, the open matrix network comprising a pharmaceutically acceptable water soluble or water-dispersible carrier material selected from partially hydrolized gelatin, dextrin, hydrolized dextrin, and alginate, and a peelable covering sheet selected from aluminum foil and aluminum foil laminate adhering to said sheet of filmy thermoplastic material so as to enclose the dosage form or forms.

7. In a process for preparing a pharmaceutical dosage form for oral administration as a solid which dosage form can rapidly be disintegrated by water, by subliming solvent from a composition comprising a pharmaceutical substance in a solvent of a pharmaceutical acceptable water-soluble or water-dispersible carrier material, the composition being in the solid state in a mold corresponding in size and shape to that of the pharmaceutical dosage form, so as to produce an open matrix network of carrier material carrying the pharmaceutical substance which matrix network is capable of being rapidly disintegrated by water, the improvement which comprises carrying out the sublimation from the solid state in a mold, being one or more depressions in a sheet of filmy material, and after the solvent is sublimed adhering a peelable covering sheet over the pharmaceutical dosage form containing depression or depressions to enclose the pharmaceutical dosage form.

8. A process as claimed in claim 7 wherein the filmy material is thermoplastic material.

9. A process as claimed in claim 7 wherein the filmy material is a polyvinylchloride film or a polyvinylchloride/polyvinylidenechloride, polyvinylchloride/polytetrafluoroethylene or polyvinylchloride/polyvinylidenechloride/polyethylene laminate.

10. A process as claimed in claim 7 wherein the covering sheet is an aluminium foil or aluminium foil laminate.

* * * * *